United States Patent [19]

Bonnet et al.

[11] Patent Number: 5,977,379
[45] Date of Patent: Nov. 2, 1999

[54] PROCESS FOR THE PREPARATION OF FLAME-RESISTANT HALOGENATED IMIDE COMPOUNDS

[75] Inventors: Evelyne Bonnet, Lamorlaye; Bernard Gurtner, Grenoble, both of France

[73] Assignee: Atochem, Puteaux, France

[21] Appl. No.: 07/854,744

[22] Filed: Mar. 19, 1992

Related U.S. Application Data

[63] Continuation of application No. 07/515,765, Apr. 13, 1990, abandoned, which is a continuation of application No. 07/194,052, May 13, 1988, abandoned.

[30] Foreign Application Priority Data

May 18, 1987 [FR] France ................................. 87 06904

[51] Int. Cl.$^6$ ..................... C07D 209/48; C07D 209/66; C07D 403/04
[52] U.S. Cl. ......................... 548/426; 548/451; 548/461; 549/246
[58] Field of Search ................... 548/426, 451, 548/461; 549/246

[56] References Cited

U.S. PATENT DOCUMENTS

| | | | |
|---|---|---|---|
| 2,420,702 | 5/1947 | Diewitt ..................................... | 548/473 |
| 3,382,254 | 5/1968 | Jenkner et al. .......................... | 549/246 |
| 3,705,127 | 12/1972 | Cyba ........................................ | 524/89 |
| 3,734,925 | 5/1973 | Minieri .................................... | 548/475 |
| 3,798,327 | 3/1974 | Minieri .................................... | 514/417 |
| 3,873,567 | 3/1975 | Cyba ........................................ | 548/451 |
| 3,959,219 | 5/1976 | Aoyama et al. ........................ | 524/101 |
| 4,003,862 | 1/1977 | Albright ................................... | 521/85 |
| 4,087,441 | 5/1978 | Lee .......................................... | 548/462 |
| 4,254,011 | 3/1981 | Bier .......................................... | 524/513 |
| 4,284,550 | 8/1981 | Mizuno et al. .......................... | 524/405 |
| 4,464,240 | 8/1984 | Hansen ................................. | 204/159.2 |
| 4,465,571 | 8/1984 | Hansen ................................. | 204/159.2 |
| 4,477,523 | 10/1984 | Biggs et al. ............................. | 428/389 |
| 5,137,948 | 8/1992 | Bonnet et al. ....................... | 548/451 X |

FOREIGN PATENT DOCUMENTS

| | | | |
|---|---|---|---|
| 0 101 785 | 3/1984 | European Pat. Off. ............... | 548/426 |
| 0101785 | 3/1984 | European Pat. Off. . | |
| 2369261 | 5/1978 | France .................................... | 548/426 |
| 410898 | 10/1966 | Switzerland ............................ | 548/426 |
| 1584202 | 2/1981 | United Kingdom ................... | 548/426 |
| 1584203 | 2/1981 | United Kingdom ................... | 548/426 |

OTHER PUBLICATIONS

Y. Takeuchi et al., Chem. Abstracts, vol. 83, No. 180336j (1975).
M. Schmidt et al, Chem. Abstracts, vol. 89, No. 164471t (1978).
Spatz et al., "Some N–Substituted Tetrabromo–phthalimide Fire Retardant Additives," Industrial and Engineering Chemistry Product Research and Development, vol. 8, No. 4 (1969), pp. 397–398.
Jones, "The Reaction of Hydrazine With Polyimides, and its Utility," Journal of Polymer Science (1969) pp. 773–784.
Drew et al., "Chemiluminescent Organic Compounds, Part I. Isomeric Simple and Complex Hydrazides of Phthalic Acid and Mode of Formation of Phthalazine and iso–Indole Rings", Journal of the Chemical Society (1937) pp. 16–36.
M. Schmidt et al., Chem. Abstracts, vol. 89, No. 164471t (1978).
J.I. Jones, "The Reaction of Hydrazine with Polyimides, and its Utility," *Journal of Polymer Science*; pp. 773–784, (1969).
Drew et al. "Chemiluminescent Organic Compounds, Part I. Isomeric Simple and Complex Hydrazides of Phthalic Acid and Mode of Formation of Phthalazine and iso Indole Rings," *Journal of the Chemical Society*, pp. 16–36 (1937).
S.M. Spatz et al., "Some N–substituted tetrabromo–phthalimide fire–retardant additives", Industrial and Engineering Chemistry Product Research and Development, vol. 8, No. 4 (1969), pp. 397–398.

*Primary Examiner*—Fiona T. Powers
*Attorney, Agent, or Firm*—Pennie & Edmonds LLP

[57] ABSTRACT

The invention relates to the preparation of halogenated imides derived from hydrazine, a halogen and a dicarboxylic acid anhydride and capable of being employed as fireproofing agents for plastics.

A dicarboxylic acid anhydride is halogenated with bromine, chlorine or a mixture thereof and then the product thus obtained is subsequently reacted with hydrazine. No prior purification or isolation of the intermediate halogenated anhydride is required.

19 Claims, No Drawings

PROCESS FOR THE PREPARATION OF FLAME-RESISTANT HALOGENATED IMIDE COMPOUNDS

This application is a Continuation of application Ser. No. 07/515,765 filed Apr. 13, 1990, abandoned, which was a Continuation of application Ser. No. 07/194,052 filed May 13, 1988, abandoned.

TECHNICAL FIELD

The present invention relates to the synthesis of flame-resistant polyhaloimide compounds and, more particularly, of imides derived from halogenated dicarboxylic acids such as tetrabromo-phthalic acid.

BACKGROUND OF THE INVENTION

Polyhaloimides, especially tetrabromophthalimides and bis(tetrabromophthalimides), are well-known compounds which may be applied as flame-retardants to many flammable materials, particularly plastics. See, for example, S. M. Spatz et al., "Some N-substituted Tetrabromophthalimide Fire-retardant Additives", *Industrial and Engineering Chemistry Product Research and Development*, Vol. 8, no. 4 (1969) pps. 397–398, as well as U.S. Pat. No. 3,873,567; French Patent no. 2,369,261 and Japanese Patent Application nos. 74-045,062 and 75-064,337.

It is also well known, however, that the preparation techniques for the polyhaloimides described in the above-mentioned references produce mediocre yields. In addition, they provide products which are yellow in color or which discolor when used. These products thus impart to the plastics in which they are incorporated (i.e. in the form of compounds or molded articles) an unacceptable color which rules out their use in a number of applications. Furthermore, these products very frequently contain materials which are volatile at the temperatures at which certain polymeric materials are molded or otherwise worked, which leads to corrosion of the molds used to form the finished article.

In addition, the organic solvents (particularly xylene, toluene, alcohol and acetic acid) used in these methods, which are most often chosen for their ability to form azeotropic mixtures with water (i.e., thus making it possible to entrain the water of condensation produced by the imidification reaction, or to dissolve the halogenated dicarboxylic acid anhydride), require the use of costly separation and recovery operations, as well as drying techniques suitable for the removal of the organic solvent vapors. The preceding disadvantages are most often encountered in the case of polyhaloimides derived from hydrazine and from halogenated carboxylic acid anhydrides.

What is more, the use of this latter raw material requires a prehalogenation of the dicarboxylic acid anhydrides. This factor represents an additional handicap both from the technological and economic standpoints, because the synthesis of these polyhaloimides requires the following additional sequence of steps:

halogenation of the carboxylic acid anhydride; and isolation and purification of the halogenated anhydride thus obtained.

SUMMARY OF THE INVENTION

It has now been found that it is not necessary to isolate and purify the intermediate halogenated anhydride. It is also not essential to employ an organic solvent to dissolve the anhydride and/or to remove the water of condensation. In fact, by operating without an organic solvent under certain conditions, it is possible to obtain, in very high yields, colorless or very slightly colored products which, without preliminary purification, are perfectly suitable for the fireproofing of macromolecular materials, including those which are used at high temperature, particularly above 250° C.

Thus, the process of the present invention comprises reacting at least one dicarboxylic acid anhydride compound such as, preferably, phthalic anhydride with a sufficient amount of a halogen to form a crude halogenated dicarboxylic acid anhydride product. By a "crude", product, applicants mean a composition comprising all of the intermediate reaction products formed by the chemical reaction, i.e., one which has not been purified to isolate a specific component, such as the halogenated anhydride thus obtained. The preferred halogens for use with the present invention ate bromine and chlorine.

The crude product containing the halogenated anhydride is thereafter reacted with a hydrazine composition, preferably in the form of a salt or a hydrate, to form a solid suspension of the halogenated imide. This suspension may then be diluted, filtered, washed to neutralize the pH of the product and then dried by conventional methods to obtain the final product.

The halogenated imides of the invention are particularly useful in providing flame-retardancy to various plastic compositions or finished products when incorporated therein in an amount of between about 5 to about 40% by weight, relative to the weight of the plastic.

DETAILED DESCRIPTION OF THE INVENTION

The process according to the invention comprises the following steps:

a) halogenating at least one dicarboxylic acid anhydride to obtain a crude halogenation product therefrom; and b) reacting the crude product with a sufficient amount of hydrazine to convert substantially all of the halogenated anhydride to the corresponding imide.

Among the anhydrides which can be employed in the present invention, those which are preferred include:

anhydrides of aromatic (e.g., benzene, naphthalene, anthracene) dicarboxylic acids, especially those having the general formula:

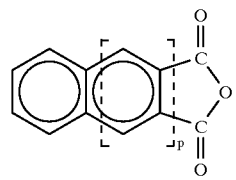

in which p is an integer ranging from 0 to 2, anhydrides of partially halogenated aromatic (e.g., benzene, naphthalene, anthracene) dicarboxylic acids, especially those having the general formula:

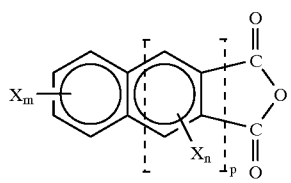

in which X is a chlorine or a bromine, m varies between 0 and 4, n varies between 0 and 2, m+n is less than 4+2p, and p varies between 0 and 2. X may also be a chlorine and a bromine when m+n greater than 1. Thus, it is possible to have combinations of chlorine and bromine in the same molecule.

In accordance with the present invention, a single anhydride or a mixture of several anhydrides may be employed. When a mixture of anhydrides is employed, one or more of them, but not all of them, may be saturated with halogen. Phthalic anhydride is preferably used in the process disclosed herein.

The halogenation of the dicarboxylic acid anhydride, i.e, step a (discussed above), may be carried out by one or more of the following methods: chlorination, bromination, or a chlorination followed by a bromination, or vice versa. Moreover, although the halogenation may be partial or total, it is preferable that it should be continued until products in which m is greater than or equal to 2 are obtained. Advantageously, a single halogen, preferably bromine, is employed in the present process.

Phthalic anhydride may be chlorinated in, for example, chlorohydrin ($HSO_3Cl$), according to the method described in German Patent no. DE 1,934,174. According to this method, a solution of phthalic anhydride in chlorohydrin is prepared, iodine is added and the mixture is heated to 120° C. The mixture is then treated with a stream of chlorine containing $ICl_3$. Phthalic anhydride can also be chlorinated in solution in oleum (i.e., fuming sulfuric acid) in the presence of iodine, by injecting chlorine into the solution. It is preferable to carry out this chlorination reaction in an oleum medium.

Alternately, bromination of a phthalic anhydride may be carried out, for example, according to the technique described in British Patent no. 1,084,375, in which the bromination occurs in a 65% oleum medium catalyzed by iodine and iron.

Moreover, in the present process, it is no longer necessary to isolate the halogenated dicarboxylic acid anhydride from the phase obtained at the end of the halogenation.

According to the process of the invention, step b is carried out by reacting the preceding phase obtained in step a with a hydrazine compound. One of the many advantages of the presently disclosed process becomes clearly apparent in this case in that it is not necessary to isolate the intermediate halogenated product obtained in step a before reacting the product with the hydrazine compound. The hydrazine compound may preferably be hydrazine itself, or hydrazine in the form of a hydrate or a hydrazine salt (for example, a sulphate, a hydrohalide or an acetate).

Further, the hydrazine compound may be employed as such or in solution with sulfuric acid. The quantity of sulfuric acid in this solution may vary within wide limits, the only condition being that it should be sufficient to ensure the appropriate dispersion of the reactants and to permit satisfactory stirring. The molar ratio of halogenated anhydride to the hydrazine compound is preferably less than about 2, and most preferably between about 1 and 2.

The reaction in step b may be carried out at atmospheric pressure at temperatures of between about 80 and 220° C., preferably between about 110 and 200° C. Further, the reaction time may be varied within wide limits, but it is generally maintained at between about 1 and 20 hours. After cooling the reaction mixture, the solid suspension thus obtained is diluted, filtered and washed with water until neutral. The product is then dried by conventional drying means.

According to a preferred embodiment of the invention, in step b, the hydrazine compound in the form of a hydrazine hydrate or hydrazinium salt is reacted with the product of step a in a sulfuric acid solution, this solution being progressively introduced into the halogenated anhydride obtained previously in step a. The quantity of sulfuric acid and its concentration are calculated so that, at the end of the addition of the hydrazine compound, the reaction mixture advantageously contains about 500 to 1,500 ml and preferably about 600 to 1,200 ml of sulphuric solution per mole of anhydride employed in step a. The concentration of this solution should be between about 80% $H_2SO_4$ and 65% oleum, and preferably between 90% $H_2SO_4$ and 40% oleum.

When step b of the subject process is carried out at a temperature of at least about 130° C., the product obtained generally consists of the bisimide corresponding to the following general structure:

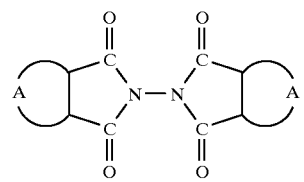

in which A denotes the residue of the halogenated anhydride employed.

The products obtained in accordance with the process according to the invention are particularly suitable as flame-retardants for use with plastics of all kinds. Their incorporation into these materials may be carried out by any known method in quantities ranging from about 5 to 40%, relative to the weight of flammable material.

EXAMPLES

The following are several illustrative examples of applicants' novel method for producing flame-resistant halogenated imide compositions. They are set forth for the purpose of illustration only, however, and should not be construed as limiting the invention in any manner.

Example 1

The following materials were successively introduced into a glass reactor equipped with a stirrer and a reflux device:

148 g of phthalic anhydride
1.5 g of iodine, and
700 g of 65% oleum

After the mixture was homogenized, it was heated to 60–70° C. and 345 g of bromine was added over 4 hours. At the end of this addition, the mixture was progressively heated for 4 hours to 110° C.

A solution of 107 g of hydrazine sulfate dissolved in 1,000 g of 96% $H_2SO_4$ was then introduced over 2 hours, while the temperature was progressively raised from 110 to 180° C. The reaction mixture was kept at this temperature for approximately 11 hours.

After cooling, dilution with water, filtering and washing the solid thus obtained until neutral, followed by a drying step, 430 g of a white solid was obtained (yield=93%). The infrared spectrum of this material corresponded to the formula:

$$\text{Br}_5\text{C}_6\text{-CO-N(CO)-N(CO)-CO-C}_6\text{Br}_5$$
(tetrabromophthalimide dimer structure)

Example 2

The following materials were successively introduced into the same apparatus as in the preceding example:

148 g of phthalic anhydride 1.5 g of iodine, and 700 g of 65% oleum

After the phthalic anhydride was dissolved, the reaction mixture was heated to 40° C., i.e., to its boiling temperature, and chlorine was introduced at the rate of 90 g/h. This introduction of chlorine was kept up for 5 hours, while the temperature was progressively raised to 130° C.

After cooling, a solution of 90 g of hydrazine sulfate in 900 g of 96% sulfuric acid was added over two hours, while being heated progressively to about 100–110° C. After the introduction of the hydrazine, the temperature was raised to 170° C. and maintained there for 11 hours.

The reaction mixture was then cooled, diluted with water, and the solid was filtered and washed until a neutral pH was reached. After drying, a white solid was obtained in a weight yield of 92%. The infrared spectrum of this material corresponded to the formula:

$$\text{Cl}_4\text{C}_6\text{(CO)}_2\text{N-N(CO)}_2\text{C}_6\text{Cl}_4$$
(tetrachlorophthalimide dimer structure)

While it is apparent that the invention herein disclosed is well calculated to fulfill the objects above stated, it will be appreciated that numerous modifications and embodiments may be devised by those skilled in the art and it is intended that the appended claims cover all such modifications and embodiments as fall within the true spirit and scope of the present invention.

We claim:

1. A process for preparing flame-resistant halogenated imide compositions which comprises:
   (a) reacting at least one dicarboxylic acid anhydride with a sufficient amount of a halogen to form a crude product comprising halogenated dicarboxylic acid anhydride and all of the intermediate products formed by the reaction, and
   (b) treating said crude products without an intervening purification step for removing said intermediate reaction products, with a sufficient amount of a hydrazine compound in an aqueous medium to convert substantially all of said halogenated dicarboxylic acid anhydride to said halogenated imide.

2. The process of claim 1 wherein said dicarboxylic acid anhydride is an anhydride of an aromatic dicarboxylic acid having the general formula:

$$\left[\begin{array}{c}\text{naphthalene-fused anhydride}\end{array}\right]_p$$

or an anhydride of a partially halogenated aromatic dicarboxylic acid having the general formula:

$$X_m\left[\begin{array}{c}\text{naphthalene-fused anhydride with } X_n\end{array}\right]_p$$

wherein, x=a chlorine or a bromine atom;

m=an integer between 0 and 4;

n=an integer between 0 and 2;

p=an integer between 0 and 2;

m+n in between 1 and less than 4+2p; and wherein, when m+n>1, X may comprise both a chlorine and a bromine atom.

3. The process of claim 2 wherein said dicarboxylic acid anhydride is phthalic anhydride.

4. The process of claim 2 wherein said halogen is bromine.

5. The process of claim 2 wherein said dicarboxylic acid anhydride comprises a mixture of at least two said anhydrides.

6. The process of claim 5 wherein X comprises both a chlorine and a bromine atom.

7. The process of claim 5 wherein at least one of said anhydrides, but not all, is saturated with a halogen.

8. The process of claim 2 wherein a sufficient amount of said halogen is reacted with said at least one dicarboxylic acid anhydride such that m is greater than or equal to 2.

9. The process of claim 1 wherein said hydrazine compound is of a hydrazine hydrate or hydrazinium salt.

10. A process for preparing flame-resistant halogenated imide compositions which comprises:
    (a) reacting at least one dicarboxylic acid anhydride with a sufficient amount of halogen to form a crude product comprising halogenated dicarboxylic acid anhydride and all of the intermediate products formed by the reaction, wherein said dicarboxylic acid anhydride comprises:
       (i) an anhydride of a dicarboxylic acid having the general formula:

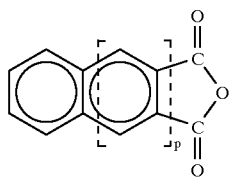

(ii) an anhydride of a partially halogenated aromatic dicarboxylic acid having the general formula:

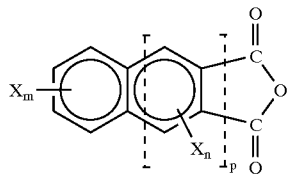

(iii) or a mixture thereof; and (b) treating said crude product, without an intervening purification step for removing said intermediate reaction products, with a hydrazine salt or a hydrazine hydrate in an aqueous medium to form a solid suspension of said halogenated imide, wherein, m=an integer between 0 and 4;
n=an integer between 0 and 2;
p=an integer between 0 and 2;
m+n is between 1 and less than 4+2p; and
x=a chlorine atom, a bromine atom or both a chlorine and a bromine atom where more than one said carboxylic acid anhydride compound is reacted with said halogenated material.

11. The process of claim 10 wherein said hydrazine salt is a sulfate, a hydrohalide or an acetate salt.

12. The process of claim 10 which further comprises dissolving a sufficient amount of a hydrazine sulfate in sulfuric acid to form a solution capable of converting substantially all of said crude product to said halogenated imide when said solution is reacted therewith.

13. The process of claim 10 wherein said hydrazine component is reacted with said crude product under atmospheric pressure at a temperature of between about 80 and 220° C.

14. The process of claim 13 wherein said reaction is carried out at a temperature of between about 110 and 200° C.

15. The process of claim 13 wherein said reaction is permitted to proceed for between about 1 to 20 hours.

16. The process of claim 10 which further comprises:
   a) diluting said solid suspension of said halogenated imide with a suitable solvent;
   b) filtering said suspension to separate said solvent from said solids;
   c) washing said solids with an aqueous solvent to neutralize the pH thereof; and
   d) drying said solids to remove substantially all said aqueous solvent from said halogenated imide.

17. A process for preparing flame-resistant halogenated imide compositions which comprises:
   (a) reacting phthalic anhydride with a sufficient amount of bromine to brominate substantially all of said phthalic anhydride and thereby forming a crude product comprising brominated phthalic anhydride and all of the intermediate products formed by the reaction;
   (b) treating said crude product, without an intervening purification step for removing said intermediate reaction products, with a solution of a hydrazine sulfate in sulfuric acid to form a solid suspension of said halogenated imide;
   (c) diluting said solid suspension of said halogenated imide with a suitable solvent;
   (d) filtering said suspension to separate said solvent from said solids;
   (e) washing said solids with an aqueous solvent to neutralize the pH thereof; and
   (f) drying said solids to remove substantially all said aqueous solvent from said halogenated imide.

18. The process of claim 10 wherein said halogen is chlorine.

19. The process of claim 10 wherein said halogen is bromine.

* * * * *